United States Patent [19]

Rabenau et al.

[11] Patent Number: 5,425,480
[45] Date of Patent: Jun. 20, 1995

[54] DOSE DISPENSER HAVING A MOLDED PLASTIC HOUSING WITH A CAVITY AND A METALLIC FOIL WALL COVERING THE CAVITY

[75] Inventors: Richard Rabenau, Birmingham; Francis E. Ryder; Stephen P. Lisak, both of Arab, all of Ala.

[73] Assignee: Ryder International Corporation, Arab, Ala.

[21] Appl. No.: 112,100

[22] Filed: Aug. 26, 1993

Related U.S. Application Data

[63] Continuation-in-part of Ser. No. 992,158, Dec. 17, 1992, abandoned.

[51] Int. Cl.6 .................................................. B67B 5/00
[52] U.S. Cl. ................... 222/153.07; 222/420; 222/541; 604/295; 206/229; 206/461
[58] Field of Search ............... 222/107, 153, 420, 541; 604/295; 206/229, 461, 467

[56] References Cited

U.S. PATENT DOCUMENTS

| | | | |
|---|---|---|---|
| 4,648,506 | 3/1987 | Campbell | 206/229 X |
| 4,871,091 | 10/1989 | Preziosi | 604/295 X |
| 4,963,045 | 10/1990 | Willcox | 222/107 X |
| 5,040,706 | 8/1991 | Davis et al. | 222/420 X |
| 5,111,932 | 5/1992 | Campbell | 206/229 X |
| 5,112,152 | 5/1992 | McBride | 206/229 X |

*Primary Examiner*—Gregory L. Huson
*Attorney, Agent, or Firm*—Trexler, Bushnell, Giangiorgi & Blackstone, Ltd.

[57] ABSTRACT

A liquid dispensing container particularly for single-use dispensing of eye medication and self-application of eye drop. The container for the liquid storage cavity has a molded plastic housing and at least one metallic foil wall secured to form an exterior wall of the housing and a flexible cavity wall. The foil wall is manually squeezable or deformable to enable a reduction in the volume of the cavity and compression and displacement of the medication therefrom. The foil wall is impervious to water vapor transmission out of the cavity which extends the shelf life of the stored container. The foil wall is also conveniently printed with labelling text and color. The plastic housing has an integrally molded nozzle which combine to control displaced flow and drop size of the dispensed medication.

32 Claims, 4 Drawing Sheets

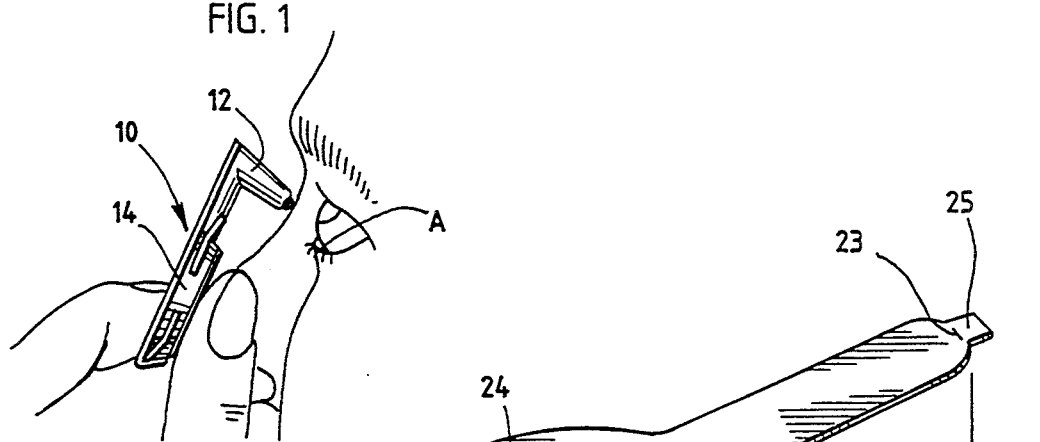
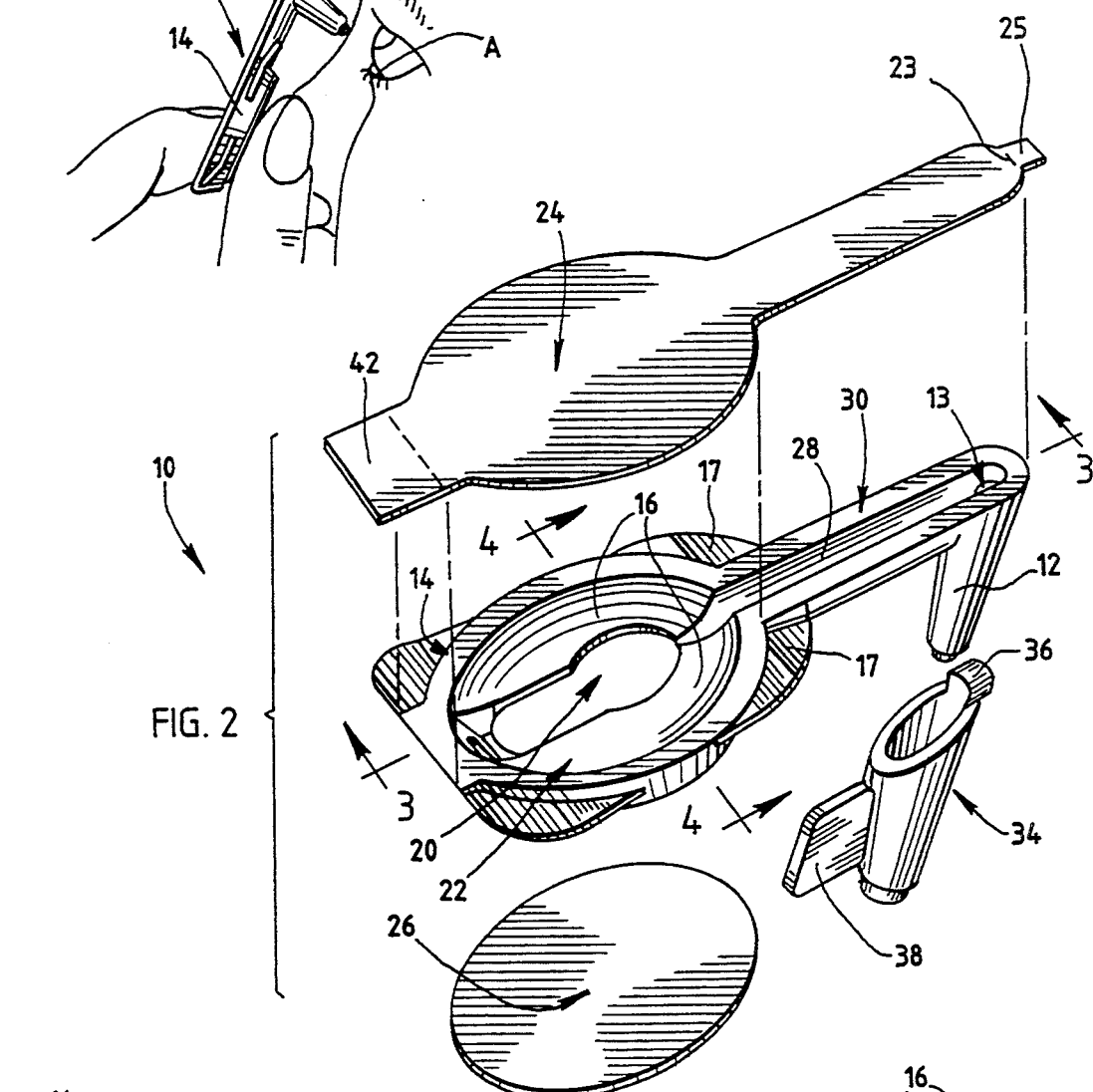
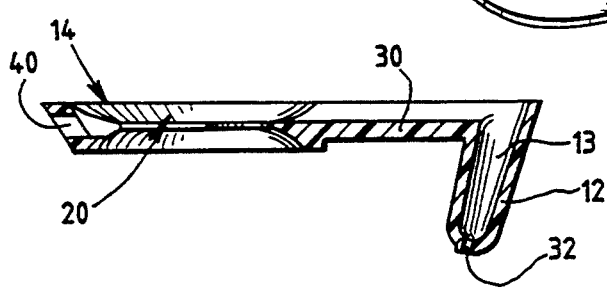
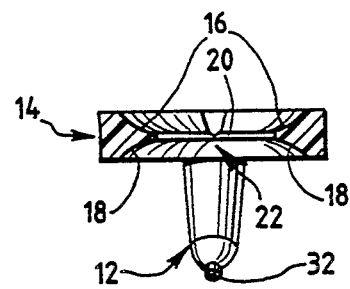

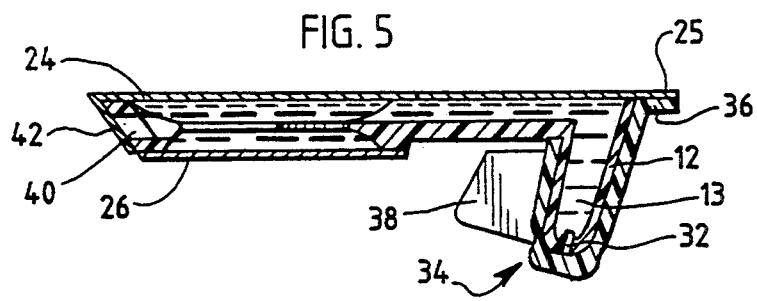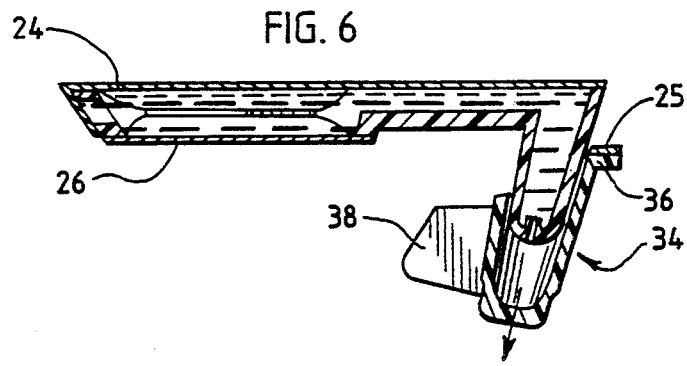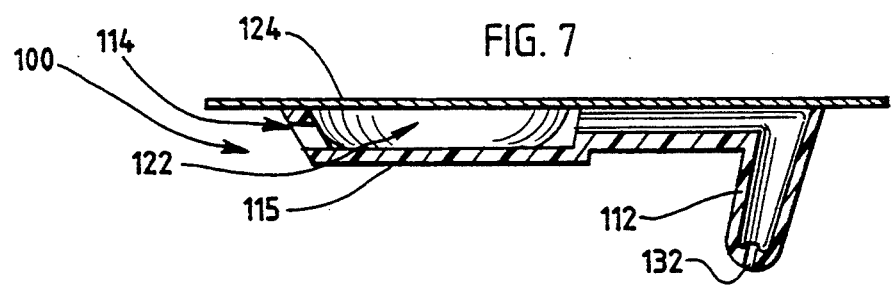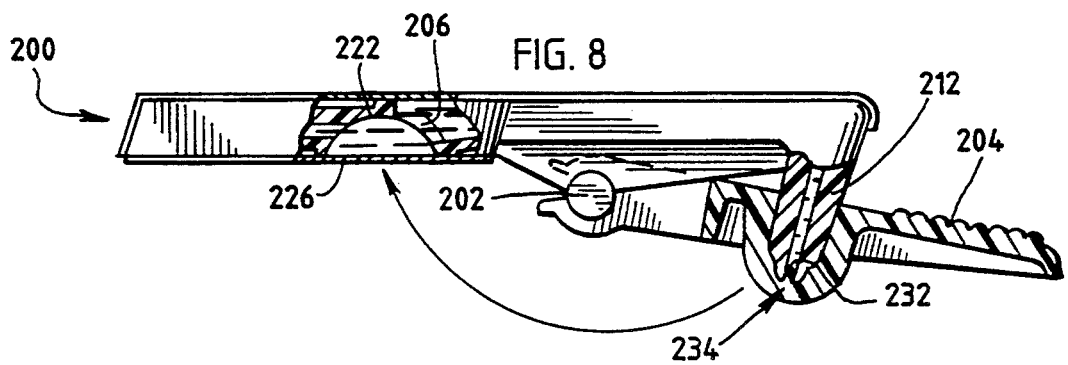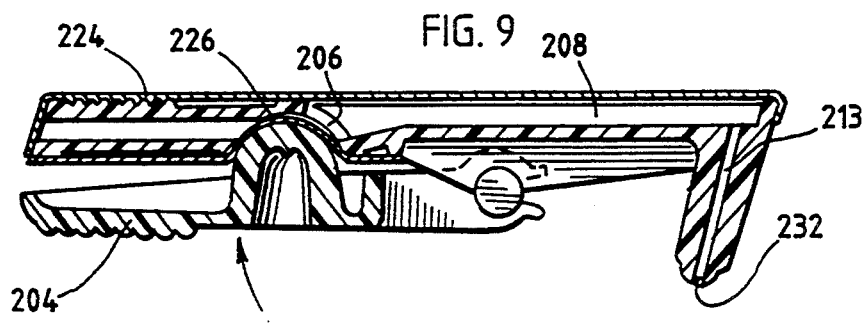

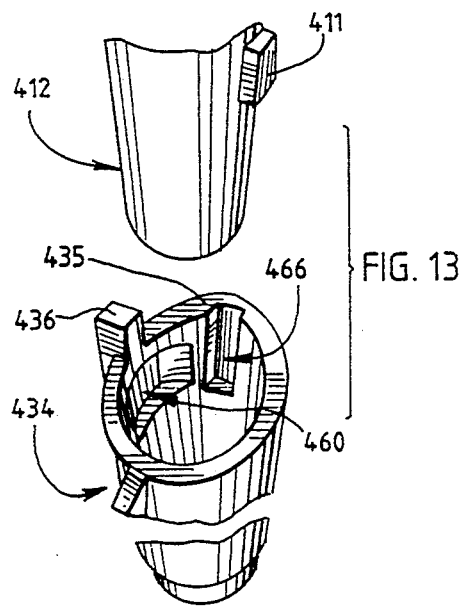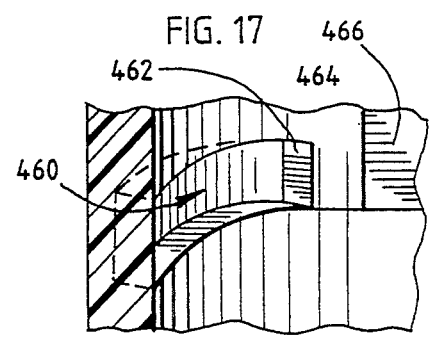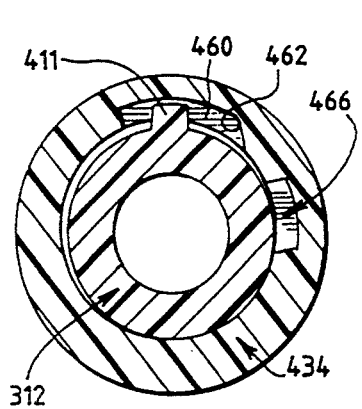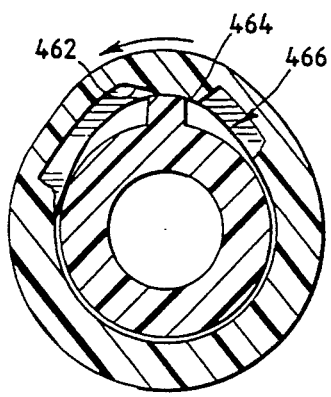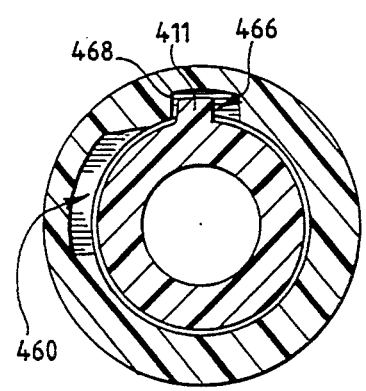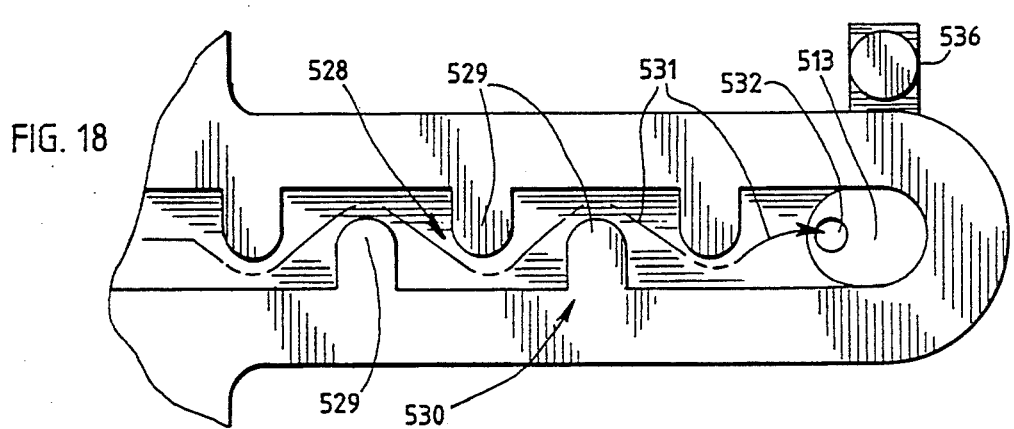

DOSE DISPENSER HAVING A MOLDED PLASTIC HOUSING WITH A CAVITY AND A METALLIC FOIL WALL COVERING THE CAVITY

CROSS REFERENCE TO RELATED APPLICATION

This application is a Continuation-in-Part of application Ser. No. 07/992,158 filed Dec. 17, 1992, now abandoned.

BACKGROUND OF THE INVENTION

The present invention relates to dispensing containers, and more particularly with respect to the illustrated embodiment relates to dispensers for the self-application of eye-drop medications.

Semi-viscus eye-drop medications for sustained release have been packaged in dispensers for self-application of the medication in the form of prefilled dispensers as described, for example, in U.S. Pat. No. 5,040,706. Such dispensers include an integral nozzle tip and a flexible plastic body of low density which can be manually squeezed to express drops from the nozzle particularly into the ocular cul-de-sac. However, the described integral container-dispensers have required prefilling with medication under sterile conditions since the flexible plastic dispensers cannot withstand autoclaving. Such dispensers also have a shelf life governed by the porosity of the thin, flexible, low density polyethylene or polypropylene from which the containers are molded which is subject to water vapor transmission loss. Furthermore, these dispensers employ a break-off cap structure resulting in a residual burr on the nozzle which interferes with proper size and direction of a dispensed drop into the eye, and the burr can also be hazardous when inadvertently contacted with the eye. Additionally, these dispensers are very difficult to mold since the integral, angled nozzle on the unitarily molded dispenser body requires both an internal core and a retractable core pin which must be perfectly aligned and mated in order to provide a continuous flow conduit and discharge port. These dual cores present problems in mating, breaking, and increased molding cycle time.

Another eye drop dispenser package is described in U.S. Pat. No. 4,871,091, in which the package walls are peeled to form a spout opening. The peeling of the walls creates potential for a torn edge at the spout discharge forming an eye hazard in dispensing the eye drops and no control over drop size and direction. These and other disadvantages are eliminated by the dispensers constructed according to the present invention.

While the present invention was developed and is disclosed herein in conjunction with a dispenser for eye medication, it is not intended that the invention be limited to this specific use. It is envisioned that there may be other uses for the dispenser where simple or limited dose applications are desired.

SUMMARY OF THE INVENTION

In accordance with the illustrated embodiment of the invention, a liquid dispensing container particularly for single-use dispensing of eye medication and self-application of eye drop is disclosed. The container includes a molded plastic housing which defines a liquid storage cavity and at least-one metallic foil wall secured to form an exterior wall of the housing and cavity. The foil wall is manually deformable to reduce the cavity volume or enable compression of and displacement of the medication therefrom and can be laminated for increased strength. The foil wall is impervious to water vapor transmission from the cavity which extends the shelf life of the stored container. The foil wall is also conveniently printed with labelling text and color.

The container also has a discharge nozzle portion integrally molded with the housing, and a closure cap removably disposed on the nozzle to seal the discharge port prior to use. Integral, open molding enables combined dimensional accuracy and contour in the cavity and nozzle discharge, to precisely control resulting drop size of dispensed medication, particularly thixotropic gel. The foil wall extends into sealing engagement with the closure cap. Removal of the closure cap retains the portion of the foil wall sealed to the cap and the resulting tear in the foil wall provides tamper evidence even when the cap is replaced.

In one embodiment, the nozzle and the closure cap include coupling structure which allows selective retention or removal of the cap for a single dispensing of the medication, but an obstruction retention structure prevents reattachment of the cap to the nozzle which discourages reuse of the dispenser and prevents potential septic danger from later reuse.

In modified embodiments, the closure cap is pivotally secured to the housing so that removal of the closure cap from the nozzle enables pivot of the cap into guided position to form a plunger which can be pressed into one of the foil walls to displace the liquid for discharged application into the eye. The guided plunging enables precisely directed squeezing of the foil wall and discharge control of the liquid displaced.

In additional embodiments, the plastic housing includes a rigid bottom wall of the container to facilitate molded contouring of the reservoir cavity to conform to a finger which promotes stability when the user presses a finger into the upper foil wall and complete displacement of the medication as the pressing finger reaches the correspondingly contoured molded lower wall of the cavity.

The housing is made from thick walls not requiring flexibility and a relatively high density thermoplastic material, such as high density polypropylene and as such can withstand autoclaving or heat sterilization temperatures. Similarly, the foil material also is of a type and kind that can withstand autoclaving. Thus, with the dispensing container of the present invention, the dispenser can be filled and heat sterilized or autoclaved after filling, which simplifies the manufacture and filling procedures vis-a-vis the prior art designs. Also, since the materials employed are of a higher density, longer shelf life is also attained, both features of which are distinct and significant advantages over the prior art.

BRIEF DESCRIPTION OF THE DRAWINGS

FIG. 1 is an elevational side view of a first embodiment of a liquid dispensing container according to the invention in position for dispensing medication therefrom into a user's eye;

FIG. 2 is an exploded perspective view of the dispensing container shown in FIG. 1;

FIG. 3 is a sectional view along a plane indicated by line 3—3 in FIG. 2;

FIG. 4 is a sectional view along a plane indicated by line 4—4 in FIG. 2;

FIG. 5 is a sectional view along a vertical plane through the assembled container shown in FIGS. 1 and 2;

FIG. 6 is a sectional view similar to FIG. 5 showing removal of a cap portion of the container;

FIG. 7 is an exploded sectional view along a vertical plane through a second embodiment of a container in accordance with the invention;

FIG. 8 is a partially sectional view along a vertical plane through a third embodiment of a container in accordance with the invention; and FIG. 9 is a sectional view similar to FIG. 8 showing pivotal movement of a combined cap and plunger member.

FIG. 13 is a fragmentary exploded view of nozzle and cap portions of a fifth embodiment of a container in accordance with the invention;

FIGS. 14–16 are sectional views showing sequential rotation of the cap for removal from the nozzle shown in FIG. 13;

FIG. 17 is a fragmentary, elevational view of the internal retention structure within the cap shown in FIG. 13; and FIG. 18 is a fragmentary, enlarged view of a discharge channel in a sixth embodiment of a container in accordance with the invention.

DESCRIPTION OF THE ILLUSTRATED EMBODIMENT

Figure 10:
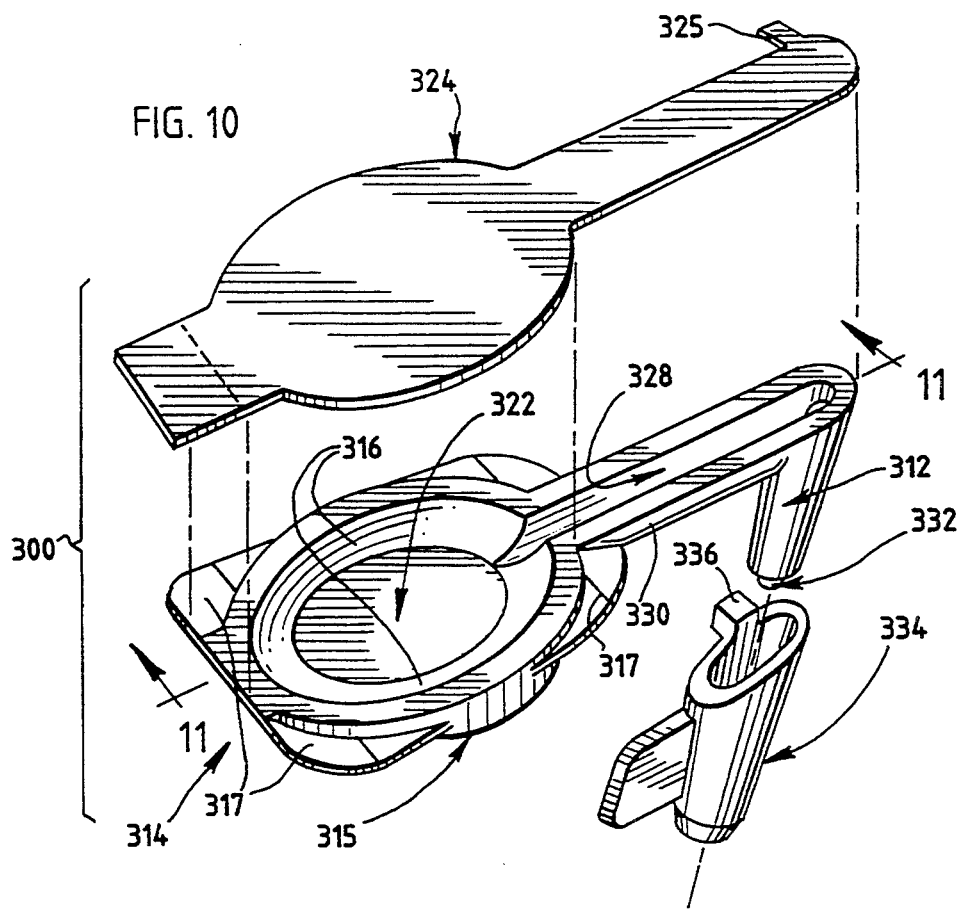
FIG. 10 is an exploded perspective view of a fourth embodiment of a container in accordance with the invention.
Figure 11:
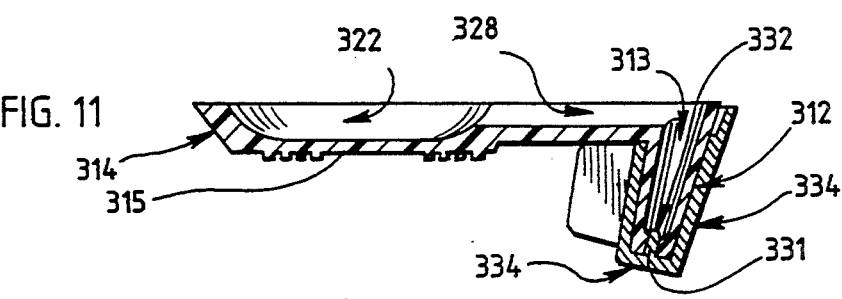
FIG. 11 is a sectional view along a plane indicated by line 11—11 in FIG. 10.

Referring to FIG. 1, a first embodiment of a dispensing container in accordance with the present invention, designated generally by a reference character 10, is shown just prior to manual squeezing thereof for self-application of liquid drops into an ocular cul-de-sac A. The container 10 has an integral nozzle 12 which forms a negative angle with the body 14 which facilitates delivery of the medication as drops into the eye while looking into a mirror and allows the user's hand to be held below the line of sight and out of the way along the cheek.

As shown in FIG. 2, the body 14 and the nozzle 12 are integrally molded preferably from plastic, for example high density polypropylene, which can be autoclaved or heat sterilized. As best shown in FIGS. 2 and 4, the body or housing 14 is molded as a frame with upper and lower curving internal walls 16 and 18 which oppositely taper inwardly and terminate to form the periphery of an internal aperture 20 as well as a contoured cavity 22 which serves as a liquid medication reservoir of single use volume for example approximately 3-7 eye drops, to prevent septic danger from attempted reuse. In the first container embodiment 10, the cavity 22 is enclosed from above and below by metallic foil walls 24 and 26 which form the respective upper and lower walls of the cavity 22. The foil walls 24 and 26 are heat sealed to the plastic body 14. The foil, for example aluminum, can be laminated for example with plastic such as polypropylene or polyester, to improve puncture resistance and general strength.

The narrow frame configuration of the body 14 serves to minimize the surface area subject to exposure to water vapor transmission through the thick, non-flexible polypropylene exterior surface, and the metallic foil walls 24 and 26 are impervious to external water vapor, thus greatly extending shelf life of the stored container. Additionally, the foil is capable of being printed with text, color or other indicia, and may be somewhat larger than the body 14 where desired, for example for increased printing. The foil walls 24 and 26 are flexible and easily squeezed with light finger pressure as depicted in FIG. 1 to reduce the volume of the reservoir cavity 22 and compress and displace the medication from the communicating conduit slot 28 formed through the bridge portion 30 which provides flow shear on thixotropic fluid, leading to the nozzle bore 13 through which the resulting liquid is discharged. Since the foil walls are squeezable, the frame body 14 and bracing ribs 17 can be rigid allowing it to be molded from plastic which will withstand autoclave or other high temperature sterilization after the medication is filled and sealed into the container 10.

The discharge nipple and port 32 from the nozzle 12 are dimensioned to promote discharge of an adequate drop size with a nozzle inclination B of approximately 75° relative to the bridge portion 30 and body 14. The smooth discharge port 32 is accurately molded without flash or burr, as described hereinafter with reference to FIG. 12, so that the discharged drop can be reliably directed with light finger pressure on the foil walls 24 and 26. The smoothly molded nipple is not hazardous should it inadvertently contact the eye during self-application.

As shown in FIGS. 2 and 5, a removable cap 34 is provided to cover the nozzle 12 and seal the discharge port 32 during storage until medication use. The cap 34 has a sealing tab 36 to which the upper foil 24 is sealed by a flap 25. The flap can be optionally molded integrally as part of the body 14. Removal of the cap 34 with a manual twisting motion facilitated by an integral flange 38, results in tearing away of the flap 25 from the foil 24 so that the flap 25 is retained on the cover tab 36 as shown in FIG. 6. If the cover 34 is subsequently replaced on the nozzle 12 in the original position of FIG. 5, the demarcation of the tear between the flap 25 and main foil 24 provides visible tamper evidence for discard. Additionally, the sealed flap 25 and tab 36 also promote secured retention of the cap 34 during container storage. Optionally, a "perf" line 23 can be fabricated to facilitate tearing of the flap 25 in cap removal.

In the embodiment illustrated in FIGS. 1–6, there is provided a filling port 40 through the end of the body 14 opening into the cavity 22 which can be sealed after filling by a seal flap 42 extending from the upper foil 24 as best shown in FIGS. 5 and 6. Alternatively, the seal flap may be formed on the lower foil 26, or it can be a separate foil component. As such, the container with the foil walls or overlays 24 and 26 in place, but with the seal flap 42 open can be delivered to the manufacturer of the medication. The medication is introduced into the cavity 22 by a filling machine and thereafter the flap 42 is closed to seal the filling port 40. The filled and sealed container 10 can be subsequently autoclaved or heat sterilized. Thus, the manufacturer of the plastic and foil components, the assembler of the components, and the filling procedures are not subjected to the rigorous sterility conditions of clean rooms as required by the Food and Drug Administration.

In use, the cap 34 is removed with the tab 38 facilitating removal. The container 10 is held and positioned as shown in FIG. 1, and the user need merely squeeze the-foil wall 24 to reduce the volume of cavity 22 and compress the medication contained in said cavity. Compression of the medication in cavity 22 will force medication out of the nozzle 12 into the user ocular cul-de-sac A. The volume of cavity 22 and the overall configuration of the container 10 is designed so that only a limited, predetermined number of drops can be dispensed. Once these are dispensed, i.e. a single dose, the container 10 is discarded. As can be appreciated, the walls 16 and 18 serve to reduce the overall volume of the cavity 22 and minimize the amount of medication remaining in the cavity 22 following dispensing, and thus serve to reduce the amount of medication discarded with the container 10.

Referring now to FIG. 7, a second embodiment 100 of a container in accordance with the invention has a lower wall 115 of plastic integrally molded with the body 114 so that only the upper wall 124 of cavity 122 is a metallic foil. The foil upper wall 124 enables sufficient manual displacement inwardly to compress the cavity 122 and expel the contained liquid medication from the nozzle 112 and discharge port 132 in drops similar to those from the first container embodiment 10.

Referring now to FIGS. 8 and 9, a third container embodiment 200 in accordance with the invention is shown. This embodiment has a cap component, comprised of a cap portion 234 and manual gripping flange 204. The cap portion 234 covers the nozzle 212 and seals the discharge port 232, said cap component 234 is pivotally mounted on a bearing pin 202 so that when the cap 234 is pivotally removed from the nozzle 212, facilitated by the gripping flange 204, continued pivotal movement will bring the rounded surface of the cap 234 into proximity to the lower foil wall 226 in preparing for application of the liquid medication. Thereafter, using the manual gripping flange 204 the cap 234 can be pressed into the foil wall 226 with light pressure on the gripping flange 204 to reduce the volume of the cavity 222 and compress and displace the medication liquid from the curved cavity 222 through the aperture 206 leading to the channel conduit 208 and nozzle bore 213 and express drop-like discharge from the port 232. The light finger application pressure is created by incorporating a mechanical advantage in the lever arm. The upper foil wall 224 need not be substantially displaced for proper expressing of the liquid.

Referring now to FIG. 10, a fourth embodiment 300 of a container in accordance with the invention has an integrally molded body 314, lower wall 315, and nozzle 312 of rigid plastic, for example high density polypropylene, which is essentially non-deformable and can be heat or steam sterilized. Peripheral bracing ribs 317 also promote rigidity as in the body 314 has a contoured cavity 322 with curving internal walls 316 which are shaped and dimensioned to conform to the contour of a finger pressing on the upper foil wall 324 so that the cavity will have no dead volume and all of the medication can be displaced. Only the actually required volume of medication to be dispensed in single use will be necessary to fill the reservoir cavity 322. The upper foil wall 324 is very pliable and allows easy deformation by a finger into the finger-contoured cavity 322 to efficiently expel the medication. The rigid body 314 provides a stable base against which the foil wall 324 is comfortably depressed to focus directed force on the viscous medication for flow through the dispensing channel 328. The upper foil wall 324 is sterilizable and can be printed on or colored, as well as serving as a moisture or vapor barrier which also resists stretching and piercing, while being selectively finger deformable. A foil side flap 325 is sealed to an aligned side tab 336 on the nozzle cap 334.

Figure 12:
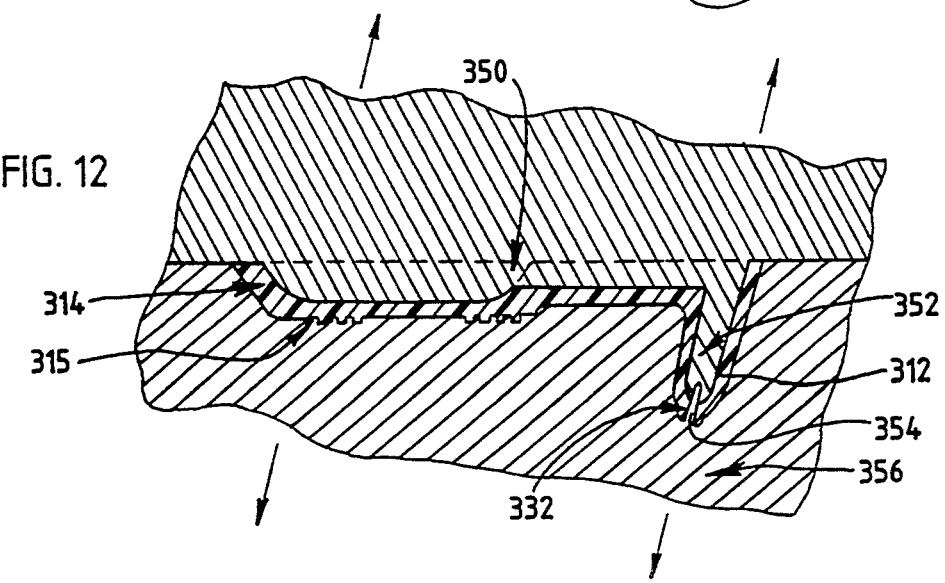
FIG. 12 is a sectional view of molds to form the plastic housing of the container shown in FIGS. 10 and 11.

Referring to FIG. 12, the body 314 can be open molded without need for a retractable core pin by instead using an upper mold 350 which has an integral, nozzle core 352 which forms the nozzle bore 313. The nozzle discharge port 332 is formed by a core pin 354 which projects upwardly through the nozzle 312 and is integral with the bottom mold 356. The core pin 354 is received within the core pin 352 at location internal to the nozzle 312 so that the discharge port 332 is smoothly molded without a mold parting line and any flash or burr. The discharge port 332 is always accurately dimensioned and delivers uniformly discharged drop size with reliably transmitted light finger pressure on the foil wall 324. The smoothly formed discharge port 332 is not hazardous if inadvertently contacted with the eye during self-application of the medication. The capped discharge port 332 is plugged and sealed by a pin 331 projecting from the cap 334.

Referring to FIGS. 13-16, a fifth embodiment has a removable cap 434 which seals the discharge port 432 during storage but also prevents replacement of the cap and any reuse of the dispenser with potential septic contamination following first use. In this embodiment, the nozzle 412 as shown in FIGS. 13-16 has a peripheral key 411 which is forced into an internally opening cam groove 460 in the cap 434 in a shoehorn manner made possible by manufacturing assembly. The groove 460 serves to lock the cap 434 on the nozzle 412 since the inserted key 411 prevents a simple longitudinal withdrawal of the cap 434 from the nozzle 412 and thus reinforces the seal of the foil wall 424 against the lateral seal tab 436 extending from the cap 434. The cam groove 460 has a generally helical configuration as shown in FIG. 17, so that removal of the cap requires a generally twisting action as illustrated by the counter rotation of the cap 434 in FIGS. 14–16. The counter rotation of the cap 434 produces riding of the helical groove 460 over the key 411 with consequent axially forced, camming, withdrawal of the cap 434 from the nozzle 412. The groove 460 has an inclined end 462 which leads twisting release of the groove 460 from the key 411 as shown in FIG. 15 so that with moderate additional twisting force on the cap 434, a buffer surface 464 at the internal radius of the cap rides over and is slightly deformed away from the key 411. Thereafter, continued rotation of the cap causes entry of the key 411 into a generally rectilinear, release slot 466 adjacent to the buffer surface 462 as shown in FIG. 16. As best shown in FIG. 13, the release slot 466 extends axially and opens through the top rim extension 435 through which the key 411 can pass to enable complete removal of the cap 434 from the nozzle 412 when the medication is to be dispensed.

If the user were to attempt to reattach the cap 434 to the nozzle 412 beginning by aligning and inserting the key 411 through the release slot 466, the rectilinear shoulder 468 of the slot 466 will abut and block the key 411 to prevent attempted clockwise twisting of the cap 434 from the position shown in FIG. 16. Thus, the cap 434 cannot be resecured to the nozzle 412 which discourages subsequent reuse of the dispenser so that the user will dispose of the dispenser after a single application of the medication, avoiding potentially septic reuse.

Referring to FIG. 18, in a sixth embodiment of a container in accordance with the invention, the conduit slot 528 leading from the reservoir cavity (not shown) to the nozzle bore 513, is convoluted through a series of flow baffles 529 which inwardly project from the walls of the housing bridge 530. The baffles 529 create additional flow resistance shear through the channel slot 528 which promotes shearing reduction in viscosity of the thixotropic fluid in the displaced flow along the tortuous path indicated by arrow 532. Transformation of the thixotropic gel in the storage cavity to liquid arriving at the nozzle discharge port 532 is accelerated by the flow turbulence through the baffled slot 528. Additionally, the baffled slot 528 will also promote mixing to reverse any settling tendency of the medication during storage in the dispensing container.

While particular embodiments of the present invention have been described herein, it will be obvious to those skilled in the art that changes and modifications in various aspects may be made without departing from the broad scope of the invention. Consequently, the scope of the invention is not limited by any particular embodiment but is defined by the appended claims and the equivalents thereof.

The invention is claimed as follows:

1. A liquid dispensing container for particular use in containing and dispensing medication in self-application as for example drops thereof into the eye, comprising: a liquid storage cavity for said medication within a container having a discharge port and including a molded plastic housing; and at least one metallic foil wall secured to said housing to define a manually displaceable wall of said cavity arranged to enable reduction in the cavity volume and the compression and expulsion of said medication from said cavity upon manual displacement of said foil wall.

2. A container according to claim 1 wherein a pair of said foil walls are secured to said housing in opposing relationship for opposing manual squeezing thereof.

3. A container according to claim 1 wherein said housing includes an integrally formed plastic wall arranged in opposing relationship to said foil wall.

4. A container according to claim 1 wherein said foil wall includes plastic material laminated therein.

5. A container according to claim 1 wherein said housing is molded from high density polypropylene.

6. A container according to claim 1 wherein said housing includes an internally projecting wall reducing volume of said cavity therein.

7. A container according to claim 1 further comprising a lever member pivotally mounted on said housing and including a displacement portion selectively pivoted to engage and deform said foil wall for said medication expulsion from said cavity.

8. A container according to claim 1 wherein said housing includes a liquid discharge nozzle in flow communication with said cavity; a closure cap removably disposed on said nozzle; and obstructing means for preventing reattaching securement of said closure cap to said nozzle after removal therefrom.

9. A container according to claim 1 wherein said housing includes a fill port therethrough and a foil panel covers said fill port.

10. A container according to claim 9 wherein said foil panel forms a portion of said foil wall.

11. A container according to claim 1 further comprising a nozzle portion including said discharge port in fluid communication with said cavity for discharge of said medication therethrough in said self-application.

12. A container according to claim 11 wherein said nozzle portion is integrally molded with said plastic housing to facilitate said self-application.

13. A container according to claim 11 wherein said nozzle portion is formed on said housing in opposing relationship relative to said secured foil wall.

14. A container according to claim 11 further comprising a closure cap removably disposed on said nozzle portion, said closure cap being pivotally mounted on said housing to enable pivot of said closure cap from said nozzle into displacing engagement against said foil wall for said medication expulsion from said cavity.

15. A container according to claim 11 further comprising a closure cap movably secured on said housing to enable movement from a first position removably disposed on said nozzle portion to a second position engaged to displace said foil wall to enable said medication expulsion from said cavity.

16. A container according to claim 11 wherein said nozzle portion and discharge port therefrom are formed to receive a closure cap removably mounted on said nozzle portion to cover and seal said discharge port thereinside prior to removal therefrom for said self-application.

17. A container according to claim 16 wherein said foil wall extends into sealing engagement with said closure cap in order to provide tamper evidence indicated by tear in said foil wall upon removal of said closure cap.

18. A container according to claim 16, wherein said closure cap includes a plug member projecting into said discharge port prior said removal.

19. A liquid dispensing container for particular use in containing and dispensing medication in self-application as for example drops thereof into the eye, comprising: a liquid storage cavity for said medication within a container including a molded plastic housing; at least one metallic foil wall secured to said housing to define a manually displaceable wall of said cavity arranged to enable reduction in the cavity volume and the compression and expulsion of said medication from said cavity upon manual displacement of said foil wall;

a nozzle portion integrally molded with said plastic housing and discharge port in fluid communication with said cavity for discharge of said medication therethrough in said self-application;

a closure cap removably disposed on said nozzle portion to seal said discharge port prior to removal therefrom for said self-application, wherein said foil wall extends into sealing engagement with said closure cap in order to provide tamper evidence indicated by tear in said foil wall upon removal of said closure cap and wherein said foil wall includes a portion thereof sealed to a tab formed on said closure cap.

20. A dispensing container construction for use in the containing and dispensing of medication in liquid or gel form, and for providing a controlled unit dosage of said medication, said container comprising: a molded plastic housing including an open cavity and a nozzle portion, with an open channel leading from said cavity to said nozzle portion; and a metallic foil wall secured to said housing and overlying both said open cavity and said open channel, which foil wall is manually displaceable to reduce the volume of said cavity and pressurize said liquid medication to expel a quantity of said medication from said nozzle.

21. A container construction according to claim 20 wherein said open cavity in said housing extends through the housing and there is provided a second metallic foil wall defining a second displaceable wall for said cavity.

22. A container construction according to claim 20, further including a fill port formed in said housing and closable by a portion of said foil wall.

23. A container construction according to claim 20 wherein said cavity is defined by housing wall portions that extend inwardly of the cavity to reduce the amount of medication remaining in said container after dispensing.

24. A container construction according to claim 20 wherein said open channel includes baffle means for promoting turbulent flow of said medication therethrough.

25. A liquid dispensing container for particular use in containing and dispensing medication in self-application as for example drops thereof into the eye, comprising: a liquid storage cavity for said medication within a container having a discharge port and including a molded plastic housing having a rigid base wall; and at least one metallic foil wall secured to said housing to define a manually displaceable wall of said cavity arranged to enable reduction in the cavity volume and the compression and expulsion of said medication from said cavity and discharge port upon manual displacement of said foil wall.

26. A container according to claim 25 wherein said rigid base wall is arranged in opposing relationship to said foil wall.

27. A container according to claim 25 further comprising a nozzle portion including said discharge port in fluid communication with said cavity for discharge of said medication therethrough in said self-application.

28. A container according to claim 27 wherein said nozzle portion is integrally molded with said plastic housing to facilitate said self-application.

29. A container according to claim 27 further comprising a closure cap removably disposed on said nozzle portion to seal said discharge port prior to removal therefrom for said self-application.

30. A container according to claim 29 wherein said foil wall extends into sealing engagement with said closure cap in order to provide tamper evidence indicated by tear in said foil wall upon removal of said closure cap.

31. A container according to claim 29 wherein said foil wall includes a portion thereof sealed to a tab formed on said closure cap.

32. A dispensing container construction for use in the containing and dispensing of medication in liquid or gel form, and for providing a controlled unit dosage of said medication, said container comprising:

a molded plastic housing including an open cavity defined by a concave wall of said housing which is contoured to the approximate curvature of a typical finger;

a nozzle portion, leading from said cavity; and a metallic foil wall secured to said housing and overlying said open cavity, which foil wall is manually displaceable to reduce the volume of said cavity and pressurize said liquid medication to expel a quantity of said medication from said nozzle, promoted by pressing a finger to displace said foil and deform said foil into conforming engagement against said concave contoured housing wall so that substantially all of said medication can be displaced from said cavity.

* * * * *